US010888762B2

(12) United States Patent
Cohen et al.

(10) Patent No.: US 10,888,762 B2
(45) Date of Patent: Jan. 12, 2021

(54) TENNIS RACKET SENSOR SYSTEM AND COACHING DEVICE

(71) Applicants: Marc A Cohen, McLean, VA (US); Alain J. Cohen, McLean, VA (US)

(72) Inventors: Marc A Cohen, McLean, VA (US); Alain J. Cohen, McLean, VA (US)

(*) Notice: Subject to any disclaimer, the term of this patent is extended or adjusted under 35 U.S.C. 154(b) by 223 days.

(21) Appl. No.: 16/213,044

(22) Filed: Dec. 7, 2018

(65) Prior Publication Data
US 2019/0134483 A1 May 9, 2019

Related U.S. Application Data

(63) Continuation-in-part of application No. 15/928,302, filed on Mar. 22, 2018, which is a continuation of application No. 14/697,248, filed on Apr. 27, 2015, now Pat. No. 9,956,469.

(60) Provisional application No. 62/084,205, filed on Nov. 25, 2014.

(51) Int. Cl.
| G09B 19/00 | (2006.01) |
| A63B 69/38 | (2006.01) |
| A63B 69/40 | (2006.01) |
| G06F 19/00 | (2018.01) |
| A63B 71/06 | (2006.01) |
| G16H 20/30 | (2018.01) |
| G16Z 99/00 | (2019.01) |

(52) U.S. Cl.
CPC ............ *A63B 69/38* (2013.01); *A63B 69/40* (2013.01); *A63B 71/0619* (2013.01); *G06F 19/00* (2013.01); *G09B 19/0038* (2013.01); *G16H 20/30* (2018.01); *G16Z 99/00* (2019.02); *A63B 2069/402* (2013.01); *A63B 2071/0683* (2013.01); *A63B 2208/0204* (2013.01); *A63B 2220/30* (2013.01); *A63B 2220/40* (2013.01); *A63B 2220/50* (2013.01); *A63B 2220/803* (2013.01); *A63B 2220/833* (2013.01); *A63B 2220/836* (2013.01)

(58) Field of Classification Search
CPC ............ G09B 19/003; G09B 19/0038; A61B 24/0003; A61B 24/0006; A61B 69/38
See application file for complete search history.

(56) References Cited

U.S. PATENT DOCUMENTS

| 6,012,995 A * | 1/2000 | Martin ............... | A63B 71/0622 473/459 |
| 2007/0105666 A1* | 5/2007 | Fernandez ......... | A63B 71/0619 473/553 |
| 2013/0053190 A1* | 2/2013 | Mettler ................. | A63B 49/00 473/463 |
| 2014/0180451 A1* | 6/2014 | Marty ................ | G06K 9/00342 700/91 |

(Continued)

*Primary Examiner* — Peter R Egloff
(74) *Attorney, Agent, or Firm* — Danielson Legal LLC

(57) ABSTRACT

Embodiments of the present invention are directed to devices, systems, and methods for implementing drills and providing coaching instructions to users. Embodiments may load a drill, measure values obtained from one or more sensors installed on a player's tennis racket and/or worn on the player's body, and use those values to detect various parameters, such as the physical impact of a ball at the player's racket. Embodiments may then output a coaching instruction to the user. Embodiments may also include adding customized coaching instructions to a drill.

20 Claims, 9 Drawing Sheets

(56) References Cited

U.S. PATENT DOCUMENTS

2014/0206481 A1* 7/2014 Zuger ................ A63B 71/0622
473/463

* cited by examiner

TENNIS RACKET SENSOR SYSTEM AND COACHING DEVICE

CROSS-REFERENCE TO RELATED APPLICATIONS

This application claims priority to pending U.S. patent application Ser. No. 15/928,302, filed on Mar. 22, 2018, which itself claims priority to U.S. patent application Ser. No. 14/697,248, filed on Apr. 27, 2015, and since issued as U.S. Pat. No. 9,956,469, which itself claims priority to U.S. Provisional Appl. No. 62/084,205, filed on Nov. 25, 2014, the entire disclosure of each of which is hereby incorporated by reference as if set forth in their entirety herein.

TECHNICAL FIELD

The present invention is related to the field of athlete performance monitoring, athletic training, and coaching. More particularly, embodiments of the present invention relate to devices, systems, and methods for loading coaching drills and detecting certain parameters relating to the impact of a tennis ball with a racket while receiving and processing event messages generated by other devices, and providing audible, visual, and/or haptic feedback, coaching prompts, and/or instructions.

BACKGROUND

It is well known in the sporting world that athletes are often intensely interested in improving their performance in a given sport. This observation is true for all levels of athletes, but it may be especially true for novice athletes who are just learning a new sport or a new skill. Some athletes learn new skills by trial and error. Other athletes receive the benefit of a trainer or instructor. Regardless of which learning process is employed, most athletes tend to go through three stages of motor skill acquisition when they are learning or improving their skills: a cognitive stage, an associative stage, and an autonomous stage.

In the cognitive stage, an athlete begins to acquire information about how to perform a new skill. The focus of the cognitive stage is the development of a mental model of movement. The athlete receives and processes new information relating to a skill and then processes that information in an attempt to cognitively understand the essential requirements and parameters of motor coordination. The cognitive stage is characterized by large gains in performance, but the performance is typically inconsistent. To improve performance consistency at this stage, techniques such as slow-motion drills, video analysis, and augmented feedback can be highly effective. It is especially important that the athlete be provided with the necessary information, guidance, and time to establish sound fundamentals of movement through cognitive processes.

In the associative stage, the learning process becomes less cognitive and more physical, as an athlete attempts to apply what he/she has learned. Here, the athlete attempts to translate cognitive knowledge into procedural knowledge. In other words, the athlete tries to transform his/her understanding about what to do into the motor knowledge of how to do it. Accordingly, there is less emphasis on processing new information at the associative stage. Instead, the athlete uses conscious processing, combined with performance feedback, to obtain better motor control. The athlete may also work at making small adjustments to various movements and stringing together short sequences of smaller movements.

In the final autonomous stage of motor acquisition, typically after years of training, physical performance can become largely automatic. Cognitive processing demands are greatly reduced, and athletes can be capable of attending to and processing other information, such as the position of opponents, game strategy, and a particular form or style of movement. This is the stage where athletes can respond almost reflexively, where they can "grip it and rip it," where they look and automatically react, and where they can enter a "zone" to achieve a state of flow.

Both good outcomes and bad outcomes are associated with the autonomous stage. Good outcomes are based on the fact that motor performance at this level requires much less cognitive demand, which thereby frees an athlete to engage in secondary tasks. On the other hand, when cognitive demand is lower, there can be more room for irrelevant and distracting thoughts. Another bad outcome during automatic motor performance is that an athlete may perpetuate incorrect movements. Just because a motor movement can be performed automatically does not mean the movement is correct or worthy of being maintained. Moreover, as soon as athletes stop thinking about a movement that was learned during the cognitive and associative stages, they may revert back to old and incorrect autonomous motor movements during competition or when they are under stress or are fatigued.

Indeed, there is always room for athletic improvement. This is true for all sports and all ages. Highly successful athletes and highly effective coaches are always looking for ways to get better. Consequently, they frequently revisit both the cognitive and associative stages of motor learning. Revisiting these stages can be essential for refining and perfecting athletic movements.

In the sport of tennis, for example, it is necessary to learn not only the rudimentary movements required to hit a ball, but also to quickly recognize, react, and respond to the movements of an opposing player. (The terms "athlete" and "player," as used herein, are intended to have the same meaning.) Indeed, an ability to recognize and react to an opponent's shot can determine whether a player is able to get in position to hit a ball, able to hit a weak defensive shot, or able to hit a strong winning shot.

A quick reaction to the movements of an opposing player can depend on an ability to anticipate, and the ability to anticipate can depend on an ability to read cues from an opposing player. Recent research has shown that one of the differences between an expert and a novice tennis player is where a player is looking (i.e., directing his/her attention) when an opponent hits the ball. In addition to a player's focus of attention, proficiency in tennis also depends on a player's efficiency of movement. Players and coaches can use many drills to improve movement efficiency. Drills can also help to train player attention and focus through proper anticipation, observation, and identification of an opponent's movements.

Without the aid of a coach it is often difficult for a player to be consistently alerted about incorrect movements or improper preparation. A player typically cannot observe their own movements and must rely on outcomes to judge whether a particular movement requires adjustment. In contrast, a third-party observer, such as a coach, can observe and analyze a player's movements as they occur independent of the outcome achieved and therefore are able to provide feedback to the player quickly after the incorrect movement occurs. However, even if coaches are utilized, they must rely on their individual comprehension of proper movements and preparation to judge their observations of a player to provide appropriate corrective feedback. Because both comprehension and observation can vary from person-to-person, corrective feedback received from coaches can be highly subjective and inconsistently provided to the player, therefore detracting from the efficiency of the player's motor skill acquisition.

Additionally, such corrective feedback is limited to verbal commands or engaging a player in visual response drills, neither of which require an athlete to react to an actual opponent. Training drills of this type are not efficient at providing immediate feedback to a player. As a result, the training benefit of such drills is not as high as it could be if appropriate feedback and cue instruction could be supplied in real time.

SUMMARY

This brief summary is provided to introduce certain concepts in a simplified form that are further described below in the Detailed Description of the Embodiments. This brief summary is not intended to identify key features or essential features of the claimed subject matter, nor is it intended to limit in any way the scope of the claimed invention.

Embodiments of the present invention are directed to devices, systems, and methods for measuring values obtained from one or more sensors installed on a player's racket, paddle, or club (hereinafter, reference will generally be made to a "racket"), and/or worn on the player's body, and using those values to calculate a number of parameters, including those related to the physical position and motion of the racket and the impact of the racket with an object, such as a ball. Embodiments of the present invention are also directed to devices, systems, and methods for receiving messages generated by other devices, including other embodiments of the present invention that are installed on rackets or worn on the bodies of other players. Embodiments of the present invention correlate the parameters and messages to generate real-time audible, visual, and/or haptic coaching prompts and other related commands and signals, for the purpose of improving certain motor skills associated with the corresponding sport.

In one aspect, embodiments relate to a first coaching device. The device includes an interface configured to load a drill including at least one first coaching instruction; receive a first input from a user to select the drill; and output the at least one first coaching instruction. The device also includes a sensor configured to measure an impact of a tennis ball on a racket, and a wireless transceiver configured to transmit at least one event message to at least one second coaching device and receive at least one event message from the at least one second coaching device, wherein the at least one second coaching device is substantially similar to the first coaching device. The device also includes a processor configured to communicate with the sensor, the wireless transceiver, and the interface; wirelessly communicate with a software application configured to receive a second user input to define the at least one first coaching instruction; add the at least one first coaching instruction to the drill; download the drill to the first coaching device; select the at least one first coaching instruction based on the measured impact or at least one received event message; instruct the wireless transceiver to transmit the at least one second event message to at least one of the at least one coaching device based on the impact of the tennis ball with the racket; and instruct the interface to output the at least one first coaching instruction.

In one embodiment, the first coaching device is configured to be worn on a wrist of the user.

In one embodiment, the drill further includes at least one second coaching instruction, the first coaching instruction corresponds to the measured impact, and the second coaching instruction corresponds to the received event message.

In one embodiment, measuring the impact includes measuring at least one of position, direction of motion, speed of motion, acceleration, vibration, and shock.

In one embodiment, the interface is configured to record at least one second coaching instruction and the processor is configured to add the at least one second coaching instruction to the drill.

In one embodiment, the processor is further configured to create and maintain a manifest of coaching instructions stored on the first coaching device, and downloading the drill to the first coaching device includes downloading only coaching instructions not already stored in the processor of the first coaching device.

In one embodiment, the processor is further configured to select the at least one first coaching instruction based on the drill.

In one embodiment, the drill defines at least one of the frequency or order at which the processor selects the at least one first coaching instruction.

In one embodiment, the coaching device is Bluetooth enabled.

In one embodiment, the output is an audio output.

In one embodiment, the coaching device further includes at least one physical press button, wherein the physical press button is configured to communicate a first data command when pressed and released by a user; and communicate a second data command when pressed continuously for at least a set duration of time by the user.

In one embodiment, the at least one coaching instruction is a pre-programmed audio command instruction.

In one embodiment, the at least one coaching instruction is outputted after a user-configurable period of time.

In another aspect, embodiments relate to a computer-implemented method for providing at least one coaching instruction via a coaching device. The method includes defining the at least one coaching instruction in a software application via a first user input; adding, via the software application, the at least one coaching instruction to a drill; wirelessly communicating the drill to a first coaching device; receiving, at the first coaching device, the drill; receiving, at the first coaching device, a second user input to select the drill; measuring, at the first coaching device, an impact of a tennis ball with a tennis racket; calculating, at the first coaching device, at least one physical parameter associated with the tennis racket; translating, at the first coaching device, the at least one physical parameter to a physical event; selecting, at the first coaching device, the at least one coaching instruction based on the physical event; outputting, at the first coaching device, the at least one coaching instruction; transmitting an event message associated with the physical event from the first coaching device to a second coaching device; receiving the event message from the first coaching device at the second coaching device; selecting, at the second coaching device, a second at least one coaching instruction based on the event message; and outputting, at the second coaching device, the second at least one coaching instruction.

In one embodiment, the method includes recording, at the first coaching device, a second coaching instruction and adding the second coaching instruction to the drill.

In one embodiment, the method includes creating and maintaining, at the first coaching device, a manifest of coaching instructions stored on the first coaching device; and wherein downloading the drill to the first coaching device includes downloading only coaching instructions not already stored on the first coaching device.

In one embodiment of the method, selecting, at the first coaching device, the at least one coaching instruction is further based on the drill.

In one embodiment, the drill defines at least one of the frequency or order at which the at least one coaching instruction is selected at the first coaching device.

In one embodiment, the drill includes a defined a duration of time during which the at least one coaching instruction is selected.

In one embodiment, the method further includes waiting for a user-configurable period of time before outputting the at least one coaching instruction.

In one embodiment, the physical event is one of a single impact, a multiple impact, and a no impact tennis swing.

In one embodiment, the at least one coaching instruction is further based on a user-selectable lesson plan.

In one embodiment, the at least one physical parameter includes at least one of position, direction of motion, speed of motion, acceleration, vibration, and shock.

In one embodiment, the at least one coaching instruction and the second at least one coaching instruction are not associated with video feedback.

In another aspect, embodiments relate to a coaching system. The coaching system includes a software application configured to: receive a first user input to define at least one coaching instruction; and add the at least one coaching instruction to a drill; and a coaching device, including: an interface configured to: load the drill including the at least one coaching instruction; receive a second user input to select the drill; and output the at least one coaching instruction; a sensor configured to measure impact of a tennis ball on a racket; a wireless transceiver configured to: transmit at least one event message to at least one other coaching device, and receive at least one event message from the at least one other coaching device, wherein the at least one other coaching device is substantially similar to the coaching device; and a processor configured to: communicate with the sensor, the wireless transceiver, and the interface; wirelessly communicate with the software application; select the at least one coaching instruction based on the measured physical impact or at least one received event message; instruct the wireless transceiver to transmit the at least one event message to at least one coaching device based on the impact of the tennis ball with the racket; and instruct the interface to output the at least one coaching instruction.

In one embodiment, the drill includes at least one first coaching instruction and at least one second coaching instruction, the first coaching instruction corresponds to the measured physical impact, and the second coaching instruction corresponds to the received event message.

In one embodiment, the processor is further configured to create and maintain a manifest of coaching instructions stored on the coaching device, and downloading the drill to the coaching device includes downloading only coaching instructions that are not already stored on the processor of the coaching device.

In one embodiment, the processor is further configured to select the at least one coaching instruction based on the drill.

In one embodiment, the drill defines at least one of the frequency or order at which the processor selects the at least one coaching instruction.

In one embodiment, the interface is further configured to record a second coaching instruction, and the processor is further configured to add the second coaching instruction to the drill.

In one embodiment, the at least one coaching instruction is outputted after a user-configurable period of time.

In one embodiment, the message event comprises a single impact, a multiple impact, and a no impact tennis swing.

In one embodiment, the at least one coaching instruction is further based on a user-selectable lesson plan.

Over time and through repetition, the varied coaching instructions provided by embodiments of the invention should help to improve the player's skill level by training the player to become better at recognizing certain opponent behaviors, to improve the performance of certain movements, and to reinforce the timing and execution of various combinations of movements in reaction to those of a vigorous opponent.

DETAILED DESCRIPTION

Figure 1A:
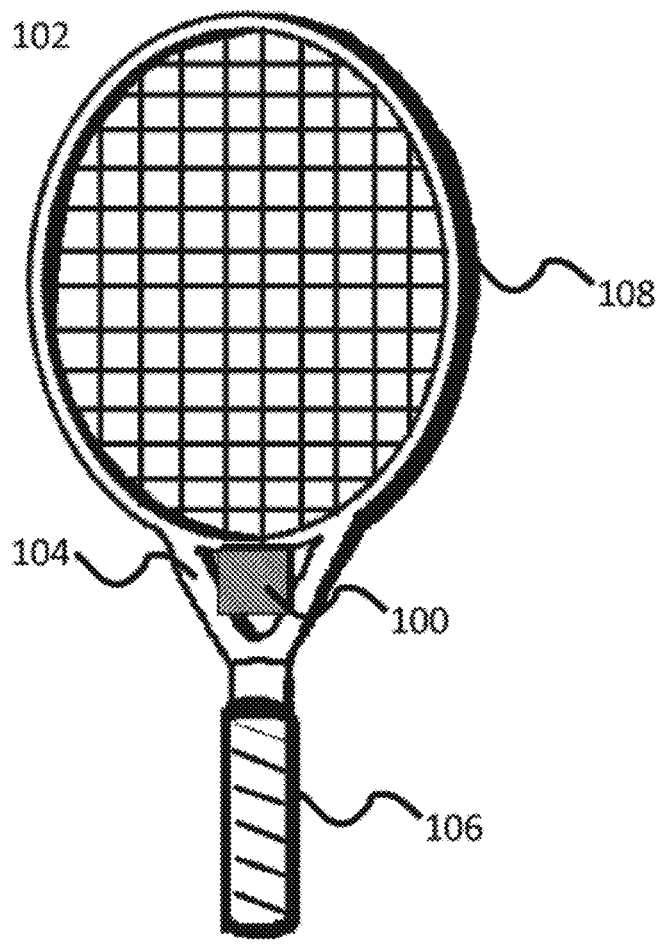
FIG. 1A illustrates a tennis racket installed with an exemplary embodiment of a device for sensing racket motion parameters, impact parameters, and providing feedback in accordance with one embodiment.

Various embodiments are described more fully below with reference to the accompanying drawings, which form a part hereof, and which show specific exemplary embodiments. However, the concepts of the present disclosure may be implemented in many different forms and should not be construed as limited to the embodiments set forth herein;

rather, these embodiments are provided as part of a thorough and complete disclosure, to fully convey the scope of the concepts, techniques and implementations of the present disclosure to those skilled in the art. Embodiments may be practiced as methods, systems or devices. The following detailed description is, therefore, not to be taken in a limiting sense.

Reference in the specification to "one embodiment" or to "an embodiment" means that a particular feature, structure, or characteristic described in connection with the embodiments is included in at least one example implementation or technique in accordance with the present disclosure. The appearances of the phrase "in one embodiment" in various places in the specification are not necessarily all referring to the same embodiment. The appearances of the phrase "in some embodiments" in various places in the specification are not necessarily all referring to the same embodiments.

Embodiments of the present invention will be described with reference to the accompanying drawings, wherein like parts are designated by like reference numerals throughout, and wherein the leftmost digit of each reference number refers to the drawing number of the figure in which the referenced part first appears. The terms "player" and "user" are used interchangeably throughout the description, and both should generally be treated as a user of embodiments.

FIG. 1A is a view of a tennis racket installed with an embodiment of a device for sensing racket position and motion parameters and providing feedback in some embodiments. The embodiment provides a coaching device 100 installed on a tennis racket 102. As illustrated, coaching device 100 is installed in the throat 104 of tennis racket 102, i.e. in the opening between the two beams of the racket that extend from the handle 106 to the head 108. In some embodiments, coaching device 100 may be attached to any part of racket 102 in a variety of ways including, for example, through the use of one or more clips, bolts, straps, bands, clamps, magnets, adhesives, or a combination thereof. In an embodiment, coaching device 100 may include a body constructed of a suitably strong but lightweight material (e.g., plastic or aluminum), and the body may house a plurality of components described in further detail below. Coaching device 100 may also be embedded within racket 102 in some embodiments. For example, coaching device 100 may be embedded within handle 106. Alternatively, if the throat of tennis racket 102 is a solid component, coaching device 100 may be embedded within the solid throat.

Figure 1B:
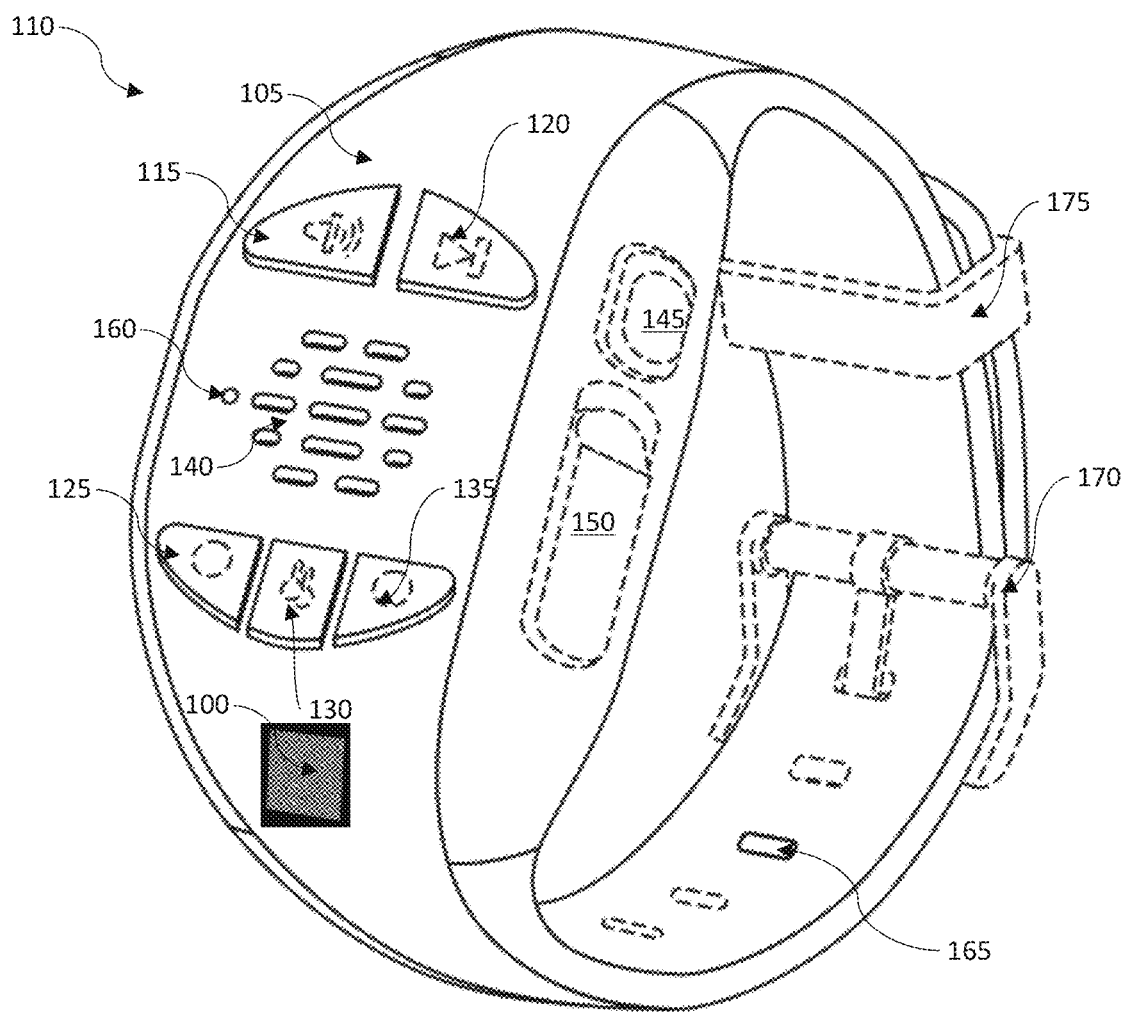
FIG. 1B illustrates a perspective view of a wearable coaching device for sensing racket motion parameters and impact parameters, enabling users to select a drill, and outputting coaching instructions in accordance with one embodiment.

FIG. 1B is a view of a wearable coaching device 110 in accordance with an embodiment. The embodiment provides a coaching device 100 installed on (e.g., via one or more clips, bolts, straps, bands, clamps, magnets, adhesives, or a combination thereof) or embedded within wearable coaching device 110. Wearable coaching device 110 may be any sort of accessory that is wearable on a player's hand or wrist, for example a bracelet, wristband, or glove. Wearable coaching device 110 may be made of any suitable material, including textile, leather, metal, plastic, rubber, wood, or a combination thereof.

In some embodiments, wearable coaching device 110 may include a band 105 configured to wrap around a user's hand or wrist. In other embodiments, the band 105 may be configured to wrap around other parts of a user's body. In some embodiments, a plurality of buttons 115-135 may be embedded or otherwise attached to the band 105. In some embodiments, each button 115-135 may have a single function. In other embodiments, buttons 115-135 may have multiple functions. A user may choose from a plurality of functions by, e.g., pressing a button 115-135 for a set duration of time or pressing a button multiple times in a row. For example, a button may have a different function if the user only presses and releases the button 115 than if the user presses and holds the button 115 down for more than approximately three seconds.

In some embodiments, button 115 may be activated to set the volume level or speak a specific coaching instruction. For example, in some embodiments, a user may press button 115 to set the volume level. The user may receive audio feedback through the speaker 140. In some embodiments, a user may press button 115 a plurality of times in quick succession to increase the volume level and/or decrease the volume level. In some embodiments, when a user presses button 115 a single time, the wearable coaching device 110 may output a noise indicting the current volume level through the speaker 140. In some embodiments, a user may press button 115 to mute the wearable coaching device 110. In some embodiments, buttons 120-135 will cease to function if the wearable coaching device 110 is muted. In some embodiments, the user may press and hold button 115 to hear a specific coaching instruction, such as a "Return" coaching instruction, wherein the user is instructed to return the ball. In some embodiments, button 115 may include an "R" symbol to show to the user that the button 115 can be used for the "Return" coaching instruction.

In some embodiments, button 120 may be activated to select a specific Drill, skip to a second Drill, and pause a Drill. For example, in some embodiments, a user may press button 120 to determine the current Drill. The user may receive audio feedback through the speaker 140. In some embodiments, a user may press button 120 a plurality of times in quick succession to skip the original selected Drill and play a subsequent Drill. In some embodiments, a user may press button 120 twice to skip to the next Drill. In some embodiments, a user may press button 120 four times to skip the currently activated Drill and the two subsequent Drills. In some embodiments, a user may press and hold button 120 to pause the currently activated Drill. A user may also press and hold button 120 multiple times to switch lessons in some embodiments.

In some embodiments, button 125 may be activated to control Bluetooth pairing and frequency of coaching instruction output. For example, in some embodiments, a user may press button 125 to set a frequency of coaching instruction output. Coaching instruction output may occur at every swing of a racket in some embodiments. In other embodiments, coaching instruction output may occur every second swing, every impact of a ball, or once every set period of time, regardless of sensor detection. In some embodiments, the frequency set may also control the number of coaching instructions output for both the user's movement and hits and the user's partner or opponent's movement and hits. In some embodiments, the wearable coaching device 110 may randomize the coaching instruction output. In some embodiments, a user may receive a plurality of coaching instructions for one movement or hit and then wearable coaching device 110 may not output coaching instructions through speaker 140 for several subsequent shots. In some embodiments, a user may press and hold button 125 to pair the coaching device 100 with a second device or an application on, for example, a mobile device. In embodiments, this pairing may occur with Bluetooth Pairing. In some embodiments, the coaching device 100 may detect when a user hits a ball with a racket, when the user's opponent or partner hits a ball with a racket, or both. In some embodiments, all three options are available on the wearable coaching device 110 and a user may cycle through the three options by repeatedly pressing button 125. In some embodiments, all three options are only available when the coaching device 100 is paired with a second coaching device 100. In some embodiments, the coaching device 100 will output audio feedback through the speaker 140 to indicate to the user if the coaching device 100 is not paired with a second coaching device 100.

In some embodiments, a user may press button 130 to set a source to trigger a command. For example, a user may press button 130 to initiate a Drill. In some embodiments, a user may press and hold button 130 to activate device-to-device pairing, wherein a first coaching device 100 on a wearable coaching device 110 may sync with a second coaching device (not pictured). This may enable a preloaded Drill to be enacted across a plurality of coaching devices 100. In some embodiments, a user may press button 130 to set the order of the coaching instructions.

In some embodiments, button 135 may be activated to set impact sensitivity or to announce a specific coaching instruction. For example, in some embodiments, a user may press button 135 to set the impact sensitivity to an intermediate level. If the coaching device 100 is unable to detect regular impacts of, for example, a tennis ball with the racket, the user may adjust the impact sensitivity with button 135 until the coaching device 100 detects the regular impacts in some embodiments. Moreover, in some embodiments, if the coaching device is unable to filter out non-impact vibration noise from impacts with, for example, the tennis ball, the user may adjust the impact sensitivity with button 135 until the coaching device 100 can filter out non-impact vibration noise. In some embodiments, the user may adjust impact sensitivity by repeatedly pressing button 135. In some embodiments, the user may receive audio feedback through speaker 140. In some embodiments, the user may press and hold button 135 to hear a specific coaching instruction, such as a "Serve" coaching instruction, wherein the user is instructed to serve the ball. In some embodiments, button 135 may include an "S" symbol to show to the user that the button 135 can be used for the "Serve" coaching instruction.

In some embodiments, a user may receive audio feedback when pressing buttons 115-135 through speaker 140. In some embodiments, a user may receive coaching instructions through speaker 140. In some embodiments, coaching device 110 may employ automatic gain control to regulate the output of audio feedback through speaker 140.

In some embodiments, the wearable coaching device 110 may have a battery life of approximately 2.5 hours. Actual duration of battery life may depend on factors including button pressing frequency and volume level. In some embodiments, the wearable coaching device 110 may be rechargeable. In some embodiments, to charge the wearable coaching device 110, the user may first turn off the wearable coaching device 110. In some embodiments, the user may press the power button 145 for a duration of time to turn off the wearable coaching device 110. In some embodiments, the user may press the power button 145 for three seconds or more to turn off the wearable coaching device 110. The user may then open the charge port 150 and plug in a charger to begin charging the wearable coaching device 110. In some embodiments, the charger may be an Android-style Micro-USB charger.

In some embodiments, to indicate that the wearable coaching device 110 is charging, an LED light 160 may blink or otherwise illuminate. In some embodiments, to indicate that the wearable coaching device 110 has finished charging, the LED light 160 may stop blinking or constantly illuminate. In some embodiments, the wearable coaching device 110 may emit a sound chime through speaker 140 to indicate that the wearable coaching device 110 is low on power. In some embodiments, the low power chime may be emitted through speaker 140 when a certain percentage of battery remains or when the wearable coaching device 110 may not be able to complete a pre-programmed Drill without first being charged. In some embodiments, the wearable coaching device 110 may report battery levels to a linked software application. In embodiments, a user may be able to check the battery level of a wearable coaching device 110 through a software application.

In some embodiments, the user may press the power button 145 for a duration of time to turn on the wearable coaching device 110. In some embodiments, the user may press the power button 145 for three or more seconds to turn on the wearable coaching device. In some embodiments, the wearable coaching device 110 will emit a sound through speaker 140 to indicate that it has been successfully powered up. For example, the wearable coaching device 110 may emit an announcement of "NeuroTennis" through speaker 140 to announce that the user has successfully powered on the wearable coaching device 110. This may also occur for any coaching device 100.

In some embodiments, a user may press the play button 120 to begin a Drill. In some embodiments, the wearable coaching device 110 can be paired with a second coaching device 100 or wearable coaching device 110 before selecting a Drill.

In some embodiments, the band 105 may be secured with a buckle 170 inserted into a hole 165. In some embodiments, the band 105 may have a plurality of holes 165 such that the band 105 is adjustable. In some embodiments, the excess length of the band 105 may be secured with a security band 175. Although FIG. 1B may show a buckle 170 as a means to secure the band 105, other embodiments may use clasps to secure the band 105 or other security means as would be recognized by one of ordinary skill in the art.

Figure 1C:
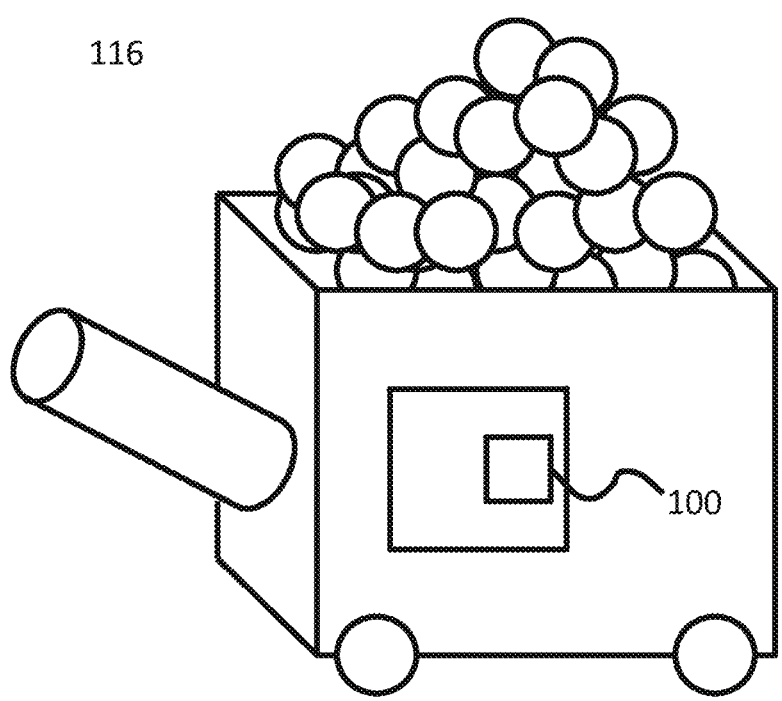
FIG. 1C illustrates a ball machine installed with an exemplary embodiment of a device for triggering the ball machine to launch balls in response to events detected at a racket in accordance with one embodiment.

FIG. 1C is a view of a ball machine 116 installed with another embodiment. In some embodiments, coaching device 100 may be connected to ball machine 116 via wired or wireless means according to well-known connection methods. Coaching device 100 may also be integrated within ball machine 116 in some embodiments. In some embodiments, coaching device 100 may share one or more components with ball machine 116, including, for example, the ball machine's power supply. Ball machine 116 may be any type of ball machine, for example a tennis ball machine, a table tennis ball machine, or a baseball or softball pitching machine in some embodiments.

Figure 2:
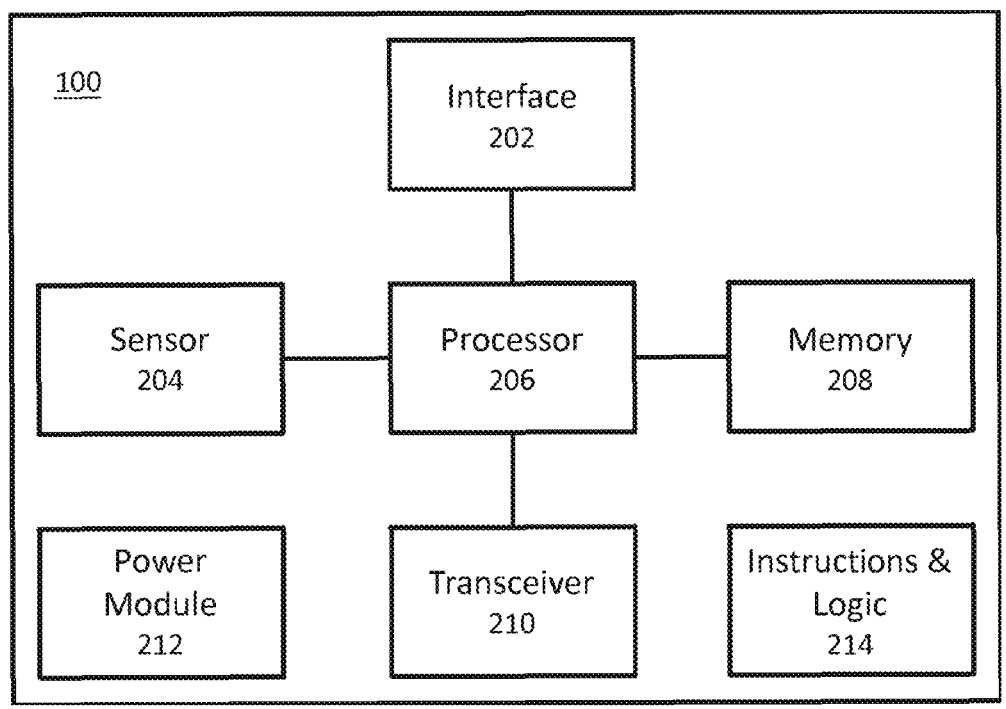
FIG. 2 is a block diagram of certain internal components of an exemplary embodiment of a device for sensing racket position, motion parameters, and impact parameters, and providing feedback in accordance with one embodiment.

FIG. 2 is a block diagram of coaching device 100. In certain operative embodiments, coaching device 100 can be installed on a racket 102 as illustrated in FIG. 1A, installed on a wearable accessory 110 as illustrated in FIG. 1B, or installed on a combination of the two. In such a combination, for example, some components may be installed on the racket 102, other components may be installed on the wearable accessory 110, and the components may share information via wireless communications. In some embodiments, as shown in FIG. 2, coaching device 100 may comprise numerous components, including one or more interface(s) 202, one or more sensor(s) 204, one or more processor(s) 206, one or more memory(ies) 208, one or more transceiver(s) 210, one or more power module(s) 212, and instructions and logic 214. In some embodiments, the one or more memory(ies) 208 may be contained on a second device, such as a mobile device or computer.

Interface 202 may comprise one or more devices for receiving input or providing output. Interface 202 can include one or more digital display(s) for outputting a text-based or graphical user interface and for receiving user input, for example via a touchscreen component. Interface 202 can also include one or more physical buttons, scroll wheels, or other conventional devices for receiving user input. In an embodiment, a player may use interface 202 to configure coaching device 100, toggle power, adjust volume, switch between various modes of operation, review metric data, and otherwise interact with coaching device 100. In some embodiments, such as the wearable coaching device 110 shown in FIG. 1B, the interface 202 may include the speaker 140 to output a coaching instruction.

In embodiments, interface 202 may include a microphone for receiving voice commands or messages. A player may, for example, use voice commands as an alternative to or in addition to using a digital display and/or buttons for interacting with coaching device 100. A microphone may also be used to record voice messages that may be sent to other embodiments.

Interface 202 may comprise one or more devices for providing coaching feedback to the player. For example, interface 202 can include one or more light(s) (e.g., light emitting diodes) 160 for providing visual feedback and/or one or more speaker(s) 140 for providing audible feedback, including coaching instructions. Interface 202 may also comprise one or more vibration motors for providing haptic feedback to the player. For example, a vibration motor like those typically found in modern mobile phones may be instructed to vibrate or "rumble" to remind a player to recover and prepare for the next shot. In embodiments, coaching feedback may be provided by any combination of one or more of the feedback devices disclosed herein.

Sensor 204 may comprise one or more device(s) for detecting and measuring a variety of physical parameters associated with coaching device 100 in some embodiments. For example, sensor 204 may include one or more accelerometer(s) for measuring one or more of the orientation, coordinate acceleration, vibration, and shock affecting coaching device 100. Sensor 204 can include any type of sensor that is capable of detecting and/or measuring physical/spatial parameters, including vibration, acceleration, speed of motion, position, shock, and direction of motion. In some embodiments, sensor 204 may be configured to detect the impact of a tennis ball with a racket. For example, a gyroscope may be used instead of or in addition to an accelerometer to measure the orientation of coaching device 100.

Processor 206 may comprise one or more devices for executing machine-readable instructions that perform one or more predetermined tasks. Processor 206 may comprise any one or a combination of hardware, firmware, and/or software. In general, processor 206 may utilize mechanical, pneumatic, hydraulic, electrical, magnetic, optical, informational, chemical, and/or biological principles, signals, and/or inputs to perform tasks. In certain embodiments, processor 206 may act upon information by manipulating, analyzing, modifying, converting, or transmitting the information for use by an executable procedure and/or an information device, and/or routing the information to an output device. Processor 206 may function as a central processing unit, local controller, remote controller, parallel controller, and/or distributed controller, etc. in some embodiments. Processor 206 may include a general-purpose device, such as a microcontroller and/or a microprocessor. In certain embodiments, processor 206 may be a dedicated purpose device, such as an Application Specific Integrated Circuit (ASIC) or a Field Programmable Gate Array (FPGA) that has been designed to implement in its hardware and/or firmware at least a part of an embodiment disclosed herein.

In some embodiments, processor 206 may communicate with the wireless transceiver 210, interface 202, and sensor 204. In some embodiments, the processor 206 may be configured to receive user input from the interface 202 to define or customize a coaching instruction; add the coaching instruction to a Drill or Lesson Plan; or select a coaching instruction based on at least one of a Calculation, Tennis Event, Physical Event, or a detected physical parameter from the sensor 204. In some embodiments, the processor 206 may receive user input from an application on a mobile device or computer through a wireless transceiver 210. In some embodiments, the processor 206 may instruct the wireless transceiver 210 to transmit at least one of the Calculation, Tennis Event, Physical Event, or a detected physical parameter from the sensor 204 to a coaching device 100. In some embodiments, the processor 206 may instruct the wireless transceiver 210 to transmit the coaching instruction to the interface 202 or to another coaching device 100. In some embodiments, the processor 206 may instruct the interface 202 to transmit the coaching instruction.

Memory 208 may be any type of apparatus known in the art that is capable of storing analog or digital information such as instructions and/or data. Examples include a non-volatile or read only memory ("ROM"), volatile or random-access memory ("RAM"), flash memory, various types of magnetic media, and the like. Memory 208 may be coupled to one or more processor(s) 206 and can store instructions and logic adapted to be executed by one or more processor(s) 206, as according to any of the embodiments disclosed herein. In some embodiments, memory 208 is integrated into the coaching device 100. In some embodiments, memory 208 is separate from the coaching device 100 and may be included in a mobile device, a computer, or a second coaching device 100.

Transceiver 210 may comprise any device, system, subsystem, or component capable of wirelessly transmitting and/or receiving information, particularly messages sent to or received from other coaching devices 100 in some embodiments. For example, transceiver 210 can include a cellular radio, RF transceiver, Bluetooth transceiver, Wi-Fi transceiver, wireless broadband transceiver (WiMAX), ZigBee transceiver, or other similar capability.

Transceiver 210 may also receive input and provide output or feedback to one or more external device(s), including ball machines, cameras, headsets, computers, tablets, mobile phones, memory sticks, and other electronic devices. In some embodiments, transceiver 210 may provide output to a camera, the output triggering the camera to record a picture or video corresponding to an event occurring on coaching device 100. In some embodiments, transceiver 210 may provide output to and receive input from a mobile phone, wherein the mobile phone permits a player to review metric data recorded by coaching device 100 and configure coaching device 100. The connection between transceiver 210 and an external device may be wireless or wired in some embodiments. In some embodiments, the user may select from both a wired or wireless connection between transceiver 210 and an external device. For wired connections, transceiver 210 may include one or more port(s) 150 accessible on or within the housing of coaching device 100.

Power module 212 may comprise one or more devices for providing electrical power to the other components of coaching device 100. Power module 212 may include one or more battery cells (e.g., lithium, alkaline, or NiMH battery cells) or other power supplies, any number of which can be electrically connected together. Some or all of the battery cells may be rechargeable. Power module 212 may also include a power input to receive input power from a power source, and a power output to provide output power to a load. In embodiments, power module 212 may store kinetic energy captured from the motion of coaching device 100 as electricity in one or more battery cell(s) and/or capacitor(s).

Instructions and logic 214 may comprise directions adapted to cause a machine, such as coaching device 100, to perform one or more particular activities, operations, or functions. The directions, which can sometimes form an entity called a "kernel", "operating system", "program", "application", "utility", "subroutine", "script", "macro", "file", "project", "module", "library", "class", "object", or "Application Programming Interface," etc., can be embodied as machine code, source code, object code, compiled code, assembled code, interpretable code, and/or executable code, etc., in hardware, firmware, and/or software. Instructions and logic 214 may reside in processor 206, in memory 208, or in another specialized device or component in some embodiments.

For ease of illustration, other components common to electrical devices have been excluded from FIG. 2. For example, a communications bus may be used to permit each of the other components to communicate with each other according to well-known techniques in some embodiments.

Having described the components of coaching device 100, attention will now be paid to its operation. For purposes of this description, reference will be made to the following terms:

Physical Event: a measurable occurrence in the physical world (e.g., a swing of a racket, a non-impact with a ball, an impact with a ball, or multiple impacts with a ball). A Physical Event may indicate the occurrence of one or more Tennis Events.

Tennis Event: a logical occurrence derived from one or more Physical Events (e.g., the start of a point, an ace serve). A Tennis Event may trigger one or more Notifications and/or Calculations.

Notification: an instruction to take some action corresponding to one or more Tennis Events (e.g., an instruction to play a recorded voice message coaching the player to focus on the point of impact). This may also include a coaching instruction.

Calculation: an instruction to calculate and/or output one or more metrics corresponding to one or more Tennis Events (e.g., an instruction to tally the number of shots in a rally).

Drill: The combination of at least one Notification and at least one Calculation and/or Tennis Event, expected to be repeated a plurality of times by a player when using a coaching device 100.

As discussed above, coaching device 100 measures values obtained from sensor 204 and calculates one or more physical parameters associated with coaching device 100. Coaching device 100 may then translate these parameters into one or more Physical Events in some embodiments. The translation process may be specified by instructions and logic 214 and performed by processor 206. In some embodiments, instructions and logic 214 may include one or more tables that map certain parameters to one or more Physical Events. For example, parameters consistent with a forehand swing may map to one Physical Event, while parameters consistent with striking a ball three times in quick succession may map to a different Physical Event.

A Physical Event may be any occurrence (or, in some embodiments, a pause between occurrences) that may be derived from measurements taken by sensor 204. For example, Physical Events can include an impact of the player's racket with a tennis ball, timed pauses between impacts, multiple closely spaced impacts, the number of steps between impacts, a physical orientation of the racket, and an acceleration of the racket.

For purposes of illustration only, an embodiment is described that includes the following specific Physical Events: Local Impact (i.e., the player strikes the ball), Remote Impact (i.e., the player's opponent strikes the ball), No Impact Swing (i.e., a swing and miss of the ball), First Pause (i.e., a pause long enough to indicate that a point or exchange has ended), Second Pause (i.e., a pause long enough after the First Pause to indicate that the next point or exchange is about to begin), Triple Local Impact (i.e., the player is preparing to serve), and Triple Remote Impact (i.e., the player's opponent is preparing to serve). Other Physical Events may be contemplated by one of ordinary skill in the art without departing from the scope of the embodiments, provided they can be mapped to one or more values and parameters.

In some embodiments, from each Physical Event, coaching device 100 may derive a corresponding Tennis Event. A Tennis Event can include any distinct event that can occur during a tennis point or Drill (e.g., serve, shot, end of point, etc.). For purposes of illustration only, an embodiment is described that includes the following specific Tennis Events: Start of Exchange, My Serve, Opponent's Serve, My Shot, Opponent's Shot, and End of Exchange. Other Tennis Events may be contemplated by one of ordinary skill in the art without departing from the scope of the embodiments.

As illustrated in Table 1, each Physical Event may map to at least one Tennis Event according to a logical correlation in some embodiments. In an embodiment, a single Physical Event may map to different Tennis Events depending on an operating mode of coaching device 100, such as a Drill Mode or a Point Mode. For example, when Point Mode is operational, a Triple Impact Physical Event indicates that the player is about to begin his or her serve and therefore maps to a Start of Point Tennis Event. A player may select an operating mode by, for example, interacting with a graphical user interface and/or one or more physical buttons provided by interface 202, as shown in FIG. 1B, or any other suitable means such as by issuing voice commands.

TABLE 1

| | Corresponding Tennis Event | |
|---|---|---|
| Physical Event | Drill Mode | Point Mode |
| Local Impact | My Shot | if first impact, My Serve, else My Shot |
| Remote Impact | Opponent's Shot | if first impact, Opponent's Serve, else Opponent's Shot |
| No Impact Swing | End of Exchange | End of Point |
| First Pause | End of Exchange | End of Point |
| Second Pause | Start of Exchange | Start of Point |
| Triple Impact | Start of Exchange | Start of Point |

In some embodiments, Tennis Events may drive a computerized model of a tennis Drill or point. In an embodiment, the computerized model may comprise a finite state machine. A finite state machine ("FSM") comprises a number of states, and the FSM is only ever in one state at a time (i.e., the "current state"). The FSM transitions from one state to another upon the occurrence of a triggering event or condition. In an embodiment, each state in the FSM corresponds to a phase of a tennis Drill or point, and the occurrence of a Tennis Event causes the FSM to either transition to a different state or repeat the same state.

Each state in the FSM may further be associated with one or more Notifications and/or one or more Calculations as defined above. In an embodiment, a Notification may include user-customizable coaching feedback, including coaching instructions. The coaching feedback can include audible feedback (e.g., tones, recorded voice messages, and/or other sound effects), visual feedback (e.g., textual or graphical messages and/or flashing LEDs), haptic feedback (e.g., vibrations), or any combination of the above. For example, a variety of methods may be used to encourage a player to keep his or her eyes focused on the point of contact between the racket and the ball. In an embodiment, a Notification includes switching on an LED for a short period of time with the occurrence of a My Shot Tennis Event to remind the player to remain focused on the point of contact. In some embodiments, as shown in FIG. 1B, the LED light 160 may be visible on the interface of the wearable coaching device 110. In some embodiments, a Notification may include playing a recorded voice message through speaker 140 shortly after the occurrence of a My Shot Tennis Event, thereby reminding the player to stay focused on the point of contact during the next shot.

Any of a variety of recorded voice messages may be played as part of a Notification in some embodiments. In some embodiments, the voice messages may be predefined and recorded by a well-known tennis professional, and/or the voice messages may be recorded by the player or the player's coach. Some example voice messages may include the following: "Keep feet moving," "Recover and split," "Turn shoulders," "Move through the shot," and "Point to the ball."

A Calculation may be any instruction to calculate and/or output (e.g., via a GUI or audible message) one or more metrics corresponding to one or more Tennis Events. In some embodiment, metrics may include one or more of the following: number of shots in a rally or point, length of time of a rally or point, transit time for a player's shot, time between shots, swing speed, power, number of steps between shots, and statistical analyses of any of the above (e.g., averages, totals, etc.). Other metrics may be contemplated by one of ordinary skill in the art without departing from the scope of the embodiments.

For example, an End of Point Tennis Event may cause a Calculation that outputs the number of shots in the most recent point. A player may also review metrics on demand, for example by using interface 202 to select a particular Calculation. In some embodiments, this selection on interface 202 may only be available on a mobile device or computer and may not be available on the wearable coaching device 110.

In embodiments, different FSMs may be associated with different operating modes. For example, FIG. 3 and FIG. 4 illustrate the phases of two FSMs when coaching device 100 is operating in a Drill Mode and a Point Mode respectively.

Figure 3:
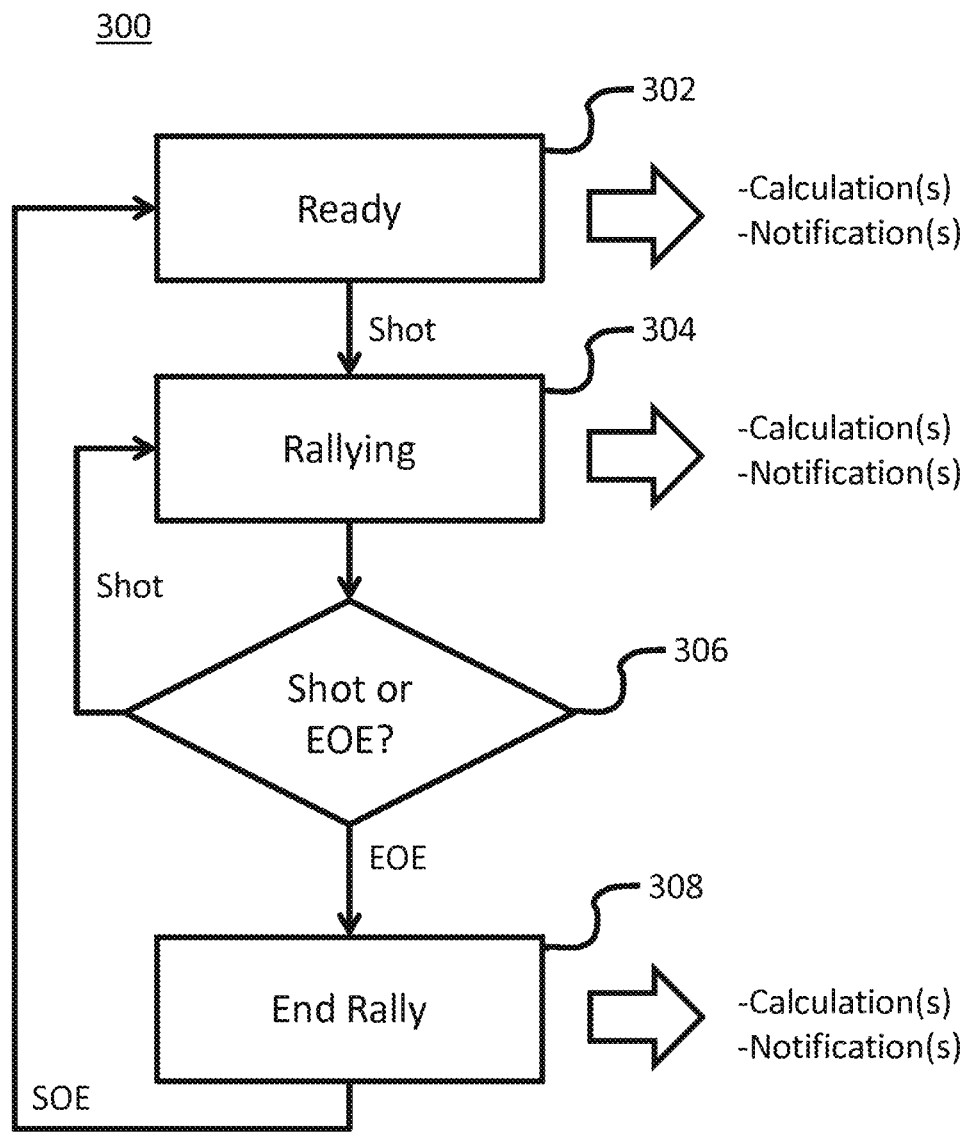
FIG. 3 is a flow chart that is representative of an exemplary embodiment of a finite state machine for associating events detected at a racket with phases of a point or drill in accordance with one embodiment.
Figure 4:
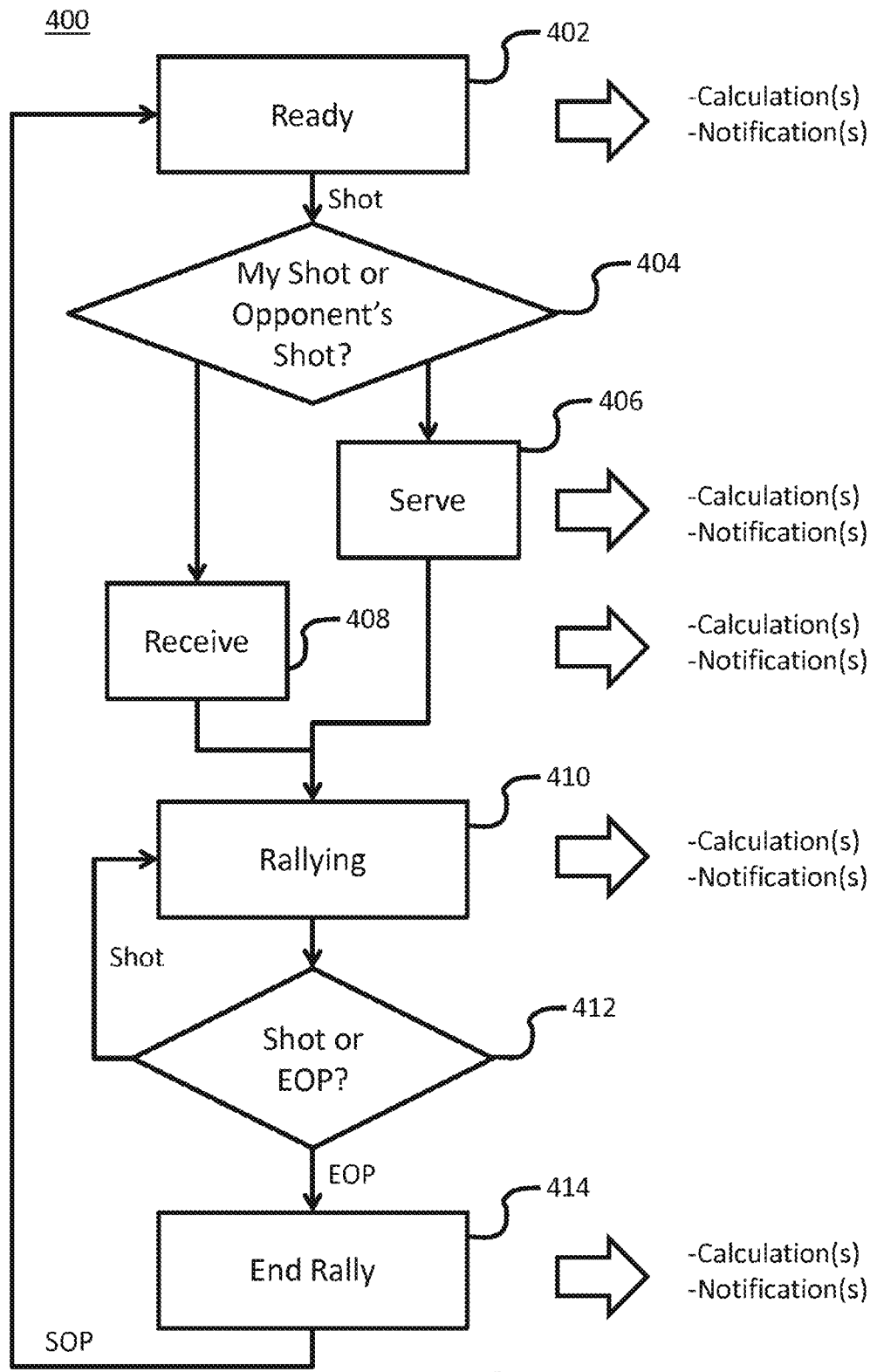
FIG. 4 is a flow chart that is representative of an exemplary embodiment of a finite state machine for associating events detected at a racket with phases of a point or drill; in accordance with one embodiment.

FIG. 3 illustrates FSM 300 for a Drill Mode embodiment. In some embodiments, FSM 300 may first enter phase 302 (a ready state or starting state) with the occurrence of a Start of Exchange ("SOE") Tennis Event. Phase 302 may be associated with one or more Calculations and/or Notifications. For example, a Calculation may include setting a shot count value to zero, and a Notification may include outputting audible feedback, including a coaching instruction, instructing the player to assume a ready stance.

In the embodiment illustrated in FIG. 3, a Local Impact or Remote Impact Physical Event may trigger a corresponding My Shot or Opponent's Shot Tennis Event, and thus cause FSM 300 to enter phase 304 (a rallying state). Like with phase 302, phase 304 may be associated with one or more Calculations and/or Notifications. For example, a Calculation may include incrementing a shot count, and a Notification may include outputting a recorded voice message instructing the player to maintain a neutral grip.

FSM 300 may repeat phase 304 each time a My Shot or Opponent's Shot Tennis Event occurs at decision 306 and enters phase 308 (end of rally) if an End of Exchange ("EOE") Tennis Event occurs at decision 306 in some embodiments. Phase 308 may also be associated with one or more Calculations and/or Notifications. For example, a Calculation may include outputting the total shot count, and a Notification may include audible feedback offering encouragement to the player, or there may be no corresponding Calculation or Notification at all. FSM 300 may loop back to phase 302 with the occurrence of an SOE Tennis Event in some embodiments.

In an embodiment, Calculations and Notifications may be associated with phases of an FSM in a manner that is instructive and relevant to the player's actions. For example, it would be of little use to output an audible Notification concerning a serve during a rallying phase. Calculations and Notifications may be configured to particular phases of an FSM in a predefined manner, or the player may customize the configurations in some embodiments. Such configurations of Calculations and Notifications may be saved as Lesson Plans that are quickly selectable and modifiable by the player. In an embodiment, coaching device 100 includes a default lesson plan for each operating mode.

A Lesson Plan is a configuration of Calculations and Notifications, containing a sequence of Drills. In an embodiment, coaching device 100 may have one or more default Lesson Plans and a player may create and edit his or her own lesson plans. Table 2 illustrates one embodiment of a sample Lesson Plan, including a name, operating mode, voice selection, and a plurality of Calculation and Notification parameters and their corresponding Tennis Events. Lesson Plans may also include a variety of other parameters.

TABLE 2

Lesson Plan Parameters

| Lesson Plan Name: | "Solid Rallying" |
| Play Mode: | "Drill" |
| Voice: | Default |

Calculation/Notification Parameters

| Tennis Event | Calculations | Notifications |
| --- | --- | --- |
| My Shot | Tally Shot Count: On<br>Record Swing Speed: On<br>Record Impact Point: Off | Announce: {"recover and split," "keep feet moving"};<br>Delay: 0.25 secs;<br>Order: Random;<br>Frequency: Every 3rd shot; |
| Opponent's Shot | Tally Shot Count: On | Announce: {"step into shot," "80% power"};<br>Delay: 0.25 secs;<br>Order: Default;<br>Frequency: Randomly every 3 shots; |
| End of Exchange | Announce: {Shot Count, Avg. Swing Speed, Avg. number of steps between shots}; | None |

TABLE 2-continued

| | Delay: 0 secs<br>Order: Default;<br>Frequency: Every time | |
|---|---|---|
| Start of Exchange | Reset Shot Count: On | None |

In some embodiments, a Lesson Plan may include a Drill associated with at least one coaching instruction. In some embodiments, a Lesson Plan may include a plurality of Drills associated with at least one coaching instruction. For example, the Drill may include detecting if the player stepped into the shot and outputting a coaching instruction announcing "step into shot" at the interface of a coaching device 100. In some embodiments, a player may first select the Drill or Lesson Plan containing the Drill at the interface of the coaching device 100. During an active Lesson Plan, the interface may output Notifications, including the coaching instruction, when a Tennis Event is detected. In embodiments, the coaching device 100 may output the Notification after the sensor detects the impact of a tennis ball with the player's racket. In other embodiments, the coaching device 100 may output the Notification at the interface when the sensor 204 detects the player swinging the racket.

In an embodiment, Calculations and Notifications may also be configured to execute instantaneously upon the occurrence of a Tennis Event, or they may be configured to execute according to a predefined and/or user-configurable amount of delay. For example, a Notification intended to instruct a player on his or her next shot may execute N seconds after the current shot, where N is a user-configurable number of seconds and/or partial seconds. Some embodiments may automatically adjust the amount of the delay based on a calculated metric of the average time between shots. Some embodiments may automatically adapt to tennis players of all skill levels.

In an embodiment where more than one Calculation and/or Notification is configured to execute with a particular phase, the player may configure the order in which the Calculations and/or Notifications execute. The order may be randomized or fixed in some embodiments. In an embodiment, only a subset of the available Calculations and/or Notifications associated with a particular phase may be executed, the subset being selected randomly (e.g., select two out of an available ten) and/or according to a schedule (e.g., where some Calculations and/or Notifications are executed every Nth time). In this manner, the player may receive a variety of coaching feedback, thereby allowing him or her to focus on multiple areas of improvement in some embodiments.

In some embodiments, a player may assign weights to Calculations and/or Notifications so that some are selected more frequently than others. For example, in some embodiments, using a scale of 1 to 3, a player could assign a 3 to Calculations and/or Notifications the player wants executed more frequently, a 2 to those the player wants executed on a regular basis, and a 1 to those the player wants executed less frequently. Other techniques may also be used to affect the order and/or frequency of Calculations and/or Notifications in some embodiments. For example, in some embodiments, a player may desire that one Notification (or even a particular coaching instruction) be outputted with every shot for a minute, and then a different Notification for the next minute, and so on.

In some embodiments, a player may create a custom Lesson Plan or Drill with a software application. In some embodiments, this software application may be loaded onto a mobile phone or computer. In some embodiments, a user may set a Tennis Event, a Calculation, and a Notification associated with the Calculation and/or Tennis Event. The Notification may include a coaching instruction to be outputted by an interface 202. In some embodiments, a player may be able to customize the Notification by selecting a light, motion, audio, or combination output. A player may also be able to record his or her voice, or the voice of his or her coach, to supply coaching feedback, including a coaching instruction. A player may also be able to change a Notification associated with a Calculation in an existing Lesson Plan or Drill at the interface 202 of a software application in some embodiments. A player may also be able to set the amount of time between the occurrence of a Tennis Event and the output of a Notification.

In embodiments, the processor 206 may be configured to communicate with the software application and download the Lesson Plan or Drill onto the memory 208 of the coaching device 100. In some embodiments, the processor 206 may be configured to wirelessly communicate with the software application. In some embodiments, the processor 206 may be configured to communicate with the software application through wired communication. In other embodiments, the processor 206 may be able to communicate with the memory 208 associated with the software application to load the Drill or Lesson Plan onto the coaching device 100. In some embodiments, the processor 206 may be configured to wirelessly communicate with the memory 208. In some embodiments, the processor 206 may be configured to communicate with the memory 208 through wired communication.

In some embodiments, the coaching device may be pre-loaded with a series of Lesson Plans and Drills. In some embodiments, these may be standard Lesson Plans and Drills. Standard Lesson Plans and Drills may be loaded on a software application in some embodiments. A user may be able to select certain standard Lesson Plans and Drills to load onto a coaching device 100. In some embodiments, a user may be able to customize Lesson Plans and Drills using a software application. In some embodiments, a user may customize the Lesson Plans and Drills by recording unique audio and video Notifications. A custom Drill may contain a combination of custom and standard Notifications. A custom Lesson Plan may contain a combination of custom and standard Drills.

FIG. 4 illustrates FSM 400 for a Point Mode embodiment. Phases 402, 406, 408, 410, and 414 may be associated with one or more Calculations and/or Notifications as discussed above. FSM 400 may enter phase 402 (a ready state or starting state) with the occurrence of a Start of Point ("SOP") Tennis Event. At decision 404, FSM 400 may transition to phase 406 (a service state) upon the occurrence of a My Shot Tennis Event or phase 408 (a receiving state) upon the occurrence of an Opponent's Shot Tennis Event in some embodiments. From either of phases 406 or 408, FSM 400 may enter phase 410 (a rallying state) upon the occurrence of a My Shot or Opponent's Shot Tennis Event in some embodiments.

In some embodiments, FSM 400 may repeat phase 410 each time a My Shot or Opponent's Shot Tennis Event occurs at decision 412 and may enter phase 414 (end of rally) if an End of Point ("EOP") Tennis Event occurs at decision 412. FSM 400 then may loop back to phase 402 with the occurrence of an SOP Tennis Event in some embodiments.

Coaching device 100 may be used in single-user embodiments or multi-user embodiments. In single-user embodiments, Tennis Events at a single coaching device 100 may drive a corresponding FSM such as FSM 300. Each state in FSM 300 may be triggered by Tennis Events at a single coaching device 100.

In multi-user embodiments, each coaching device 100 may maintain its own FSM (e.g., an FSM 300 or FSM 400), but the FSM may be affected by Tennis Events at other coaching devices 100. For example, two coaching devices may each be executing FSM 400, and both begin in the ready phase 402. When a My Shot Tennis Event occurs at one coaching device 100, it may wirelessly transmit the My may Tennis Event to the other coaching device 100 (e.g., via its transceiver 210) where it will be received and interpreted as an Opponent's Shot Tennis Event in some embodiments. In some embodiments, each coaching device 100 may transmit each Tennis Event to each other coaching device 100, thereby ensuring that the FSMs at each coaching device 100 are synchronized. In some embodiments, each coaching device 100 is substantially similar to the other coaching devices 100.

In an embodiment, Tennis Events may be transmitted in the form of messages, and each message may include an identification of the coaching device transmitting the message along with information about the Tennis Event. Such information may include the type of Tennis Event (e.g., a "My Shot" Tennis Event) as well as information about the type of shot (e.g., speed, spin, direction, etc.). For example, a coaching device 100 may determine that a player hit a forehand lob shot based on the speed and direction of the shot (e.g., as measured by sensor 204), and the corresponding message may include this information, thereby enabling a receiving coaching device 100 to generate a relevant Notification (e.g., an announcement to prepare for an overhead shot).

In alternative embodiments, messages may include measurement information gathered directly from sensor 204 and/or information about a Physical Event instead of or in addition to information about the Tennis Event. In such embodiments, the receiving coaching device 100 translates the measurement information into Physical Events and derives corresponding Tennis Events in the same manner as the transmitting device.

In multi-user embodiments, coaching device 100 may also operate according to a singles player mode or a doubles player mode. For example, two opponents in a singles match may each configure their respective coaching devices 100 to operate in a singles player mode, meaning alternating shots are expected by the FSM (e.g., a My Shot Tennis Event followed by an Opponent's Shot Tennis Event). Two teammates in a doubles match, on the other hand, may each configure their respective coaching device 100 to operate in a doubles player mode, meaning that only one shot per team is expected by the FSM. For example, when two teammates are operating coaching devices 100 in a doubles player mode, the FSM 400 at each coaching device 100 may recognize a My Shot Tennis Event regardless of which player hits the ball in some embodiments.

In multi-user embodiments, two or more coaching devices 100 may establish a communication session using a conventional "handshake" or other suitable discovery/connection mechanism. For example, a player using one coaching device 100 may initiate a discover function at coaching device 100 that seeks out other coaching devices 100 broadcasting their availability. Password authentication or other suitable mechanisms may be employed to ensure that only authorized coaching devices 100 may join a communication session.

Figure 5A:
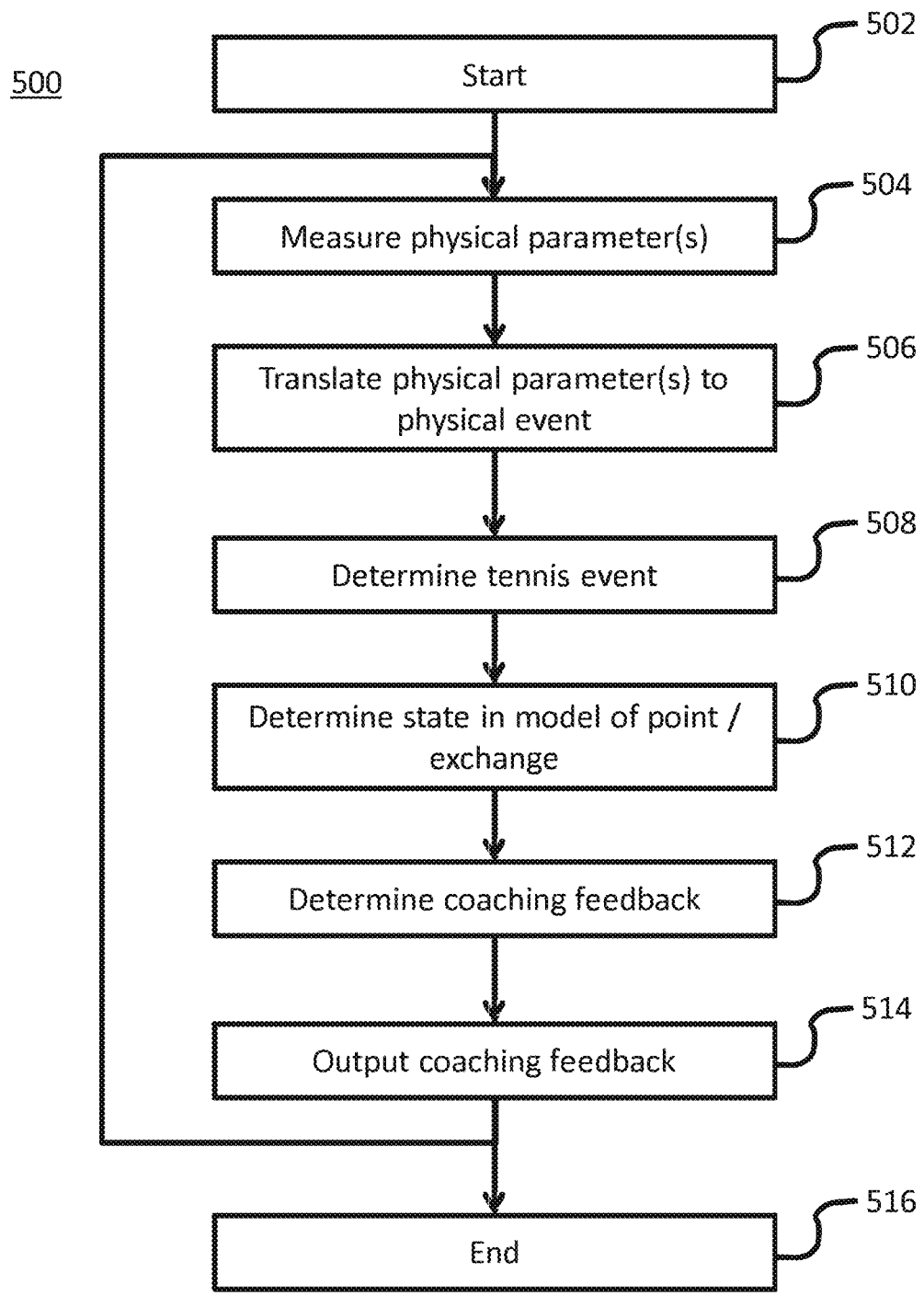
FIG. 5A illustrates an exemplary single-user method for providing feedback in accordance with one embodiment.
Figure 5B:
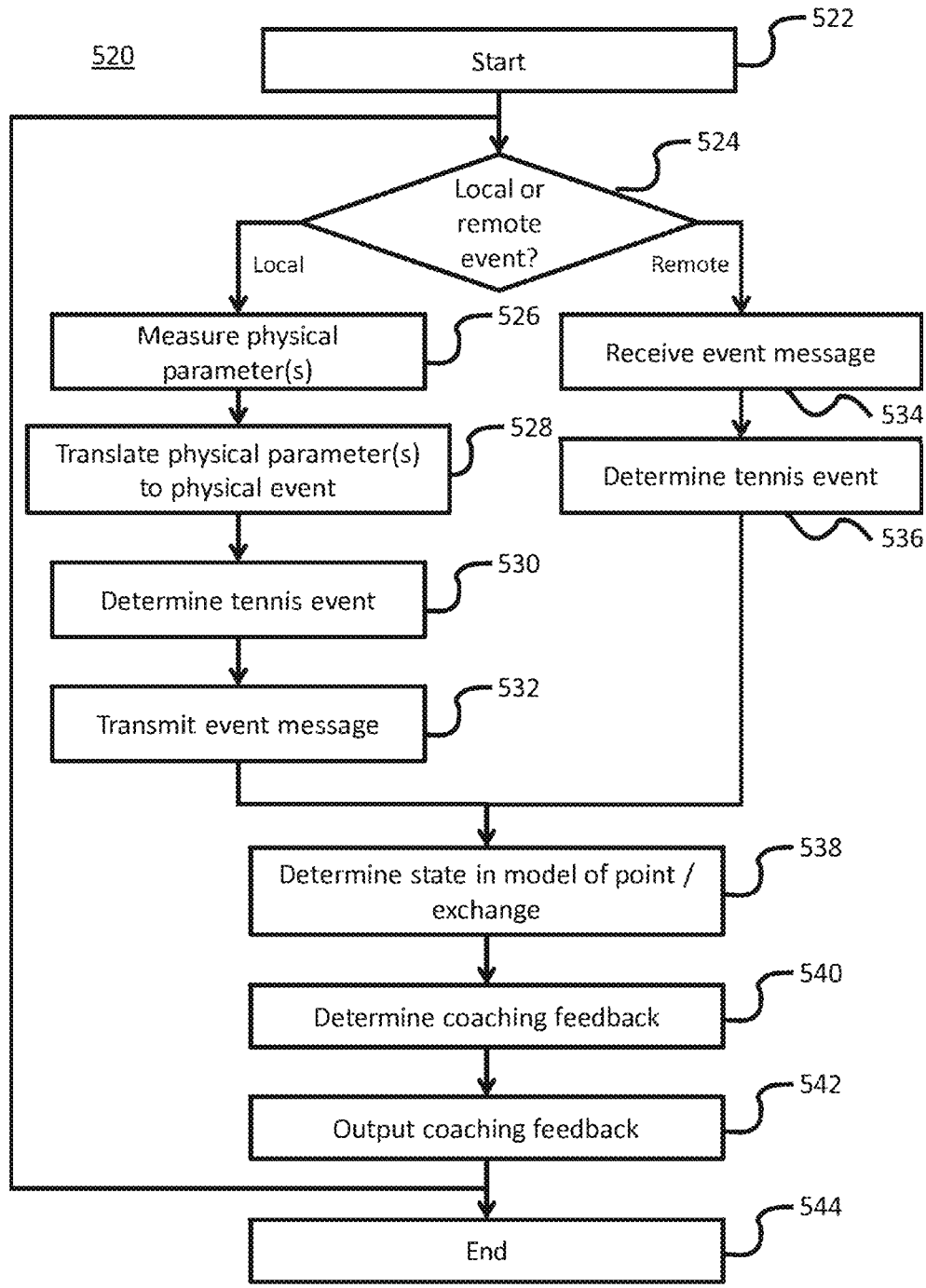
FIG. 5B illustrates an exemplary multi-user method for providing feedback in accordance with one embodiment.

FIG. 5A and FIG. 5B, respectively, illustrate a single-user method 500 and a multi-user method 520 for providing feedback to a user in some embodiments. Method 500 may begin at step 502. A player may, for example, initiate method 500 by powering on his or her coaching device 100 using the power button 145 and selecting a Drill. In some embodiments, point mode is also available to the user for selection. In some embodiments, the name of the current Drill will automatically be output through the speaker 140. A user may choose to select the current Drill by pressing the button 120. In some embodiments, a user may also choose to pause the Drill by pressing the button 120. In some embodiments, if a user has not pressed the button 120 within a short period of time, such as under five seconds, pressing the button 120 once may cause the name of the Drill to be outputted through the speaker 140. In some embodiments, a user may hold the button 120 to pause the Drill. The user may also press the button 120 to resume the Drill. In some embodiments, a user may press the button 120 a plurality of times to skip a Drill. In some embodiments, the interface 202 may output an instruction through the speaker 140 to press and hold the button 120 to skip a Drill. In some embodiments, the coaching device 100 may circulate through all loaded Drills, such that if there are five Drills and Drill four is currently selected, the user may press button 120 three times to play Drill one.

At step 504, coaching device 100 measures values obtained from sensor 204 and calculates one or more physical parameters (e.g., parameters corresponding to the position and/or motion of the player's racket). At step 506, coaching device 100 translates the physical parameters into a Physical Event (e.g., a swing of a racket or an impact with a ball). At step 508, coaching device 100 determines a Tennis Event (e.g., the start of a point) based on the Physical Event in the previous step. At step 510, coaching device 100 determines a corresponding state (e.g., a rallying state) in a model (e.g., a finite state machine) of a Drill or point based on the Tennis Event in the previous step. At step 512, coaching device 100 determines coaching feedback, including a coaching instruction, (e.g., a Notification and/or a Calculation) that corresponds to the determined state in the previous step. At step 514, coaching device 100 outputs the coaching feedback (e.g., via one or more of audible, visual, and haptic feedback). In some embodiments, if the player finishes a Drill or game or wishes to switch to a different mode, method 500 may end at step 516. In some embodiments, method 500 may return to step 504.

In some embodiments, the coaching device 100 may emit a sound, light, and/or motion signal to indicate to at least one user that the Drill is halfway complete. In some embodiments, the coaching device 100 may emit a sound, light, and/or motion signal to indicate to at least one user that the Drill is one minute away from completion. The user may have the opportunity to extend the Drill by a period of time, such as two minutes, by pressing the button 120 after receiving the signal. In some embodiments, the user must press the button 120 within five seconds of receiving the signal to extend the Drill time.

Method 520 begins at step 522. As with method 500, a player may, for example, initiate method 520 by powering on his or her coaching device 100 and selecting a Drill or point mode. At step 524, coaching device 100 either detects a local event (e.g., an event detected at the player's racket) or a remote event (e.g., an event received from the player's opponent). For local events, at step 526, coaching device 100 measures values obtained from sensor 204 and calculates one or more physical parameters (e.g., parameters corresponding to the position and/or motion of the player's racket). Then, at step 528, coaching device 100 translates the physical parameters into a Physical Event (e.g., a swing of a racket or an impact with a ball). At step 530, coaching device 100 determines a Tennis Event (e.g., the start of a point) based on the Physical Event in the previous step. At step 532, coaching device transmits an event message based on the Tennis Event to another coaching device 100.

For remote events, at step 534, coaching device 100 receives an event message from another coaching device 100. At step 536, coaching device 100 determines a Tennis Event (e.g., the start of a point) based on the event message received in the previous step.

For both local and remote events, at step 538, coaching device 100 determines a corresponding state (e.g., a rallying state) in a model (e.g., a finite state machine) of a Drill or point based on the Tennis Event in one of step 532 or step 536. At step 540, coaching device 100 determines coaching feedback (e.g., a Notification and/or a Calculation) that corresponds to the determined state in the previous step. At step 542, coaching device 100 outputs the coaching feedback (e.g., via one or more of audible, visual, and haptic feedback). In some embodiments, if the player finishes a Drill or game or wishes to switch to a different mode, method 520 ends at step 544. In some embodiments, method 520 returns to step 524.

As illustrated in FIG. 1C, embodiments of coaching device 100 may interface with a ball machine 116. In such an embodiment, one or more players with coaching devices 100 may practice with a ball machine 116 as if they were playing or practicing with a human opponent or coach. A coaching device 100 connected to a ball machine 116 may maintain an FSM in the same manner as a coaching device 100 used by a player in some embodiments. In essence, a coaching device 100 connected to a ball machine may be thought of as a coaching device 100 used by another player in a multi-user embodiment, i.e., it transmits and receives messages concerning Tennis Events and other related information, and such Tennis Events drive a corresponding FSM. The primary difference is that Notifications trigger actions at the ball machine (e.g., launching the next ball) instead of outputting coaching feedback.

For example, a player with a coaching device 100 may initiate a Start of Exchange Tennis Event by hitting her racket with her hand three times. The player's coaching device 100 may then transmit the Start of Exchange Tennis Event to the ball machine's 116 coaching device 100 where a corresponding Notification may trigger the ball machine 116 to launch a ball in some embodiments. A rally between the player and the ball machine 116 may then proceed according to an FSM (e.g., FSM 400), with each of the player's shots being interpreted as an Opponent's Shot Tennis Event and triggering a Notification and subsequent launch of another ball at ball machine 116 in some embodiments.

Various parameters at ball machine 116 may be user-configured or established in pre-defined lesson plans designed for ball machine 116. For example, ball machine 116 may be configured to launch balls with varying speed, spin, direction, delay, etc., or to set up different types of shots for the player (e.g., forehand, backhand, overhead smash, etc.), according to the selected Lesson Plan in some embodiments. In some embodiments, a player's coaching device 100 may communicate with ball machine 116 to execute a synchronized Drill or Lesson Plan. In this manner, coaching device 100 and ball machine 116 execute the same Drill or Lesson so that ball machine 116 can launch a ball according to particular parameters (e.g., to set up a player's forehand shot), and the player's coaching device 100 may be configured to output coaching instructions corresponding to those parameters (e.g., instructions on how to prepare for a forehand shot).

Similar to multi-user embodiments, a player with a coaching device 100 establishes a communication session with ball machine 116 using a conventional "handshake" or other suitable discovery/connection mechanism. The player may also use her coaching device 100 to configure ball machine 116 (e.g., to select a synchronized Drill or Lesson) and/or control other aspects of ball machine 116 in some embodiments.

In an embodiment, Tennis Events derived by coaching device 100 may also or alternatively be communicated to an observer, for example a coach with a tablet, computer, or mobile device running an application and communicating with coaching device 100 via transceiver 210. As with multi-user and ball machine embodiments, Tennis Events are communicated via messages and may be accompanied by other information such as metrics. Such an embodiment may enable an observer to review metrics and other information about the player in real-time. In the same or an alternative embodiment, a coaching device 100 may receive real-time Notifications and/or Calculations from the observer. For example, the observer may select one or more Notifications using the application on his or her device for transmission to coaching device 100, which may then execute the Notifications immediately or at a time determined by a Lesson Plan.

In some embodiments, the observer may speak into a microphone on his or her device, and the observer's voice may be transmitted to coaching device 100 for immediate announcement or at a time determined by a Lesson Plan. Such an embodiment, for example, may permit a coach to instruct a player from a distance without having to shout and potentially disturb others. Similarly, in an embodiment, the player may speak into a microphone included in or connected to interface 202 in coaching device 100, and the player's voice may be transmitted via transceiver 210 to the observer, coach, and/or another player. For example, coaching device 100 may be configured to record and transmit a player's voice in response to the player pressing a button on coaching device 100 or speaking a voice command. In some embodiments, coaching device 100 may act as a two-way radio, thereby permitting players to communicate with other players and coaches without having to shout.

In an embodiment, players may also speak voice commands to interact with ball machine 116. In such an embodiment, interface 202 may receive the voice commands and transmits them via transceiver 210 to the coaching device 100 connected to the ball machine 116. The coaching device 100 at the ball machine 116 may then instruct the ball machine accordingly. For example, a player may command the ball machine 116 to launch a shot or a particular type of shot, or to stop launching shots altogether in accordance with a selected Lesson Plan.

In embodiments, Tennis Events may be communicated to other types of devices. For example, coaching device 100 may communicate a Tennis Event message to a camera that is programmed to take pictures or video of the player upon the occurrence of certain Tennis Events.

In other embodiments, the coaching device 100 used by a first player may pair with a second coaching device 100 used by a second player. The second player may be the opponent of the first player or a partner of the first player. In embodiments, more than two devices may also be synchronized together in a similar manner. To pair coaching devices 100 for partner play, a player may first press the button 130 to enable device to device pairing. The second player may also press button 130 on the coaching device 100 of the second player. If the connection between the first coaching device 100 and the second coaching device 100 is successful, either or both coaching devices 100 may output a signal indicating the successful connection. For example, the coaching device 100 may vibrate or output a "Connected" audio output through the speaker 140. In some embodiments, if the coaching devices 100 are not paired in under a specific period of time, such as a minute, the coaching device 100 may automatically stop attempting to pair with a second coaching device 100.

In some embodiments, a first user and a second user may select the same Drill or Lesson Plan with their coaching devices 100. The first coaching device 100 may measure the impact of a tennis ball with a racket at the sensor and then may calculate a physical parameter, such as a vibration, associated with the racket. The first coaching device may then translate the calculated physical parameter to a Tennis Event, such as a serve and output the calculated Notification associated with the Tennis Event. In embodiments, the first coaching device 100 may transmit an event message associated with the Tennis Event to a second coaching device 100 with a wireless transceiver 210. The second coaching device 100 may then receive the event message with the second wireless transceiver 210 and may output a second Notification associated with receiving the event message. For example, if the first user hit the ball and the event message was sent to the coaching device of the second user, the second user may hear the phrase "line up your body" before swinging at the incoming tennis ball.

Figure 6:
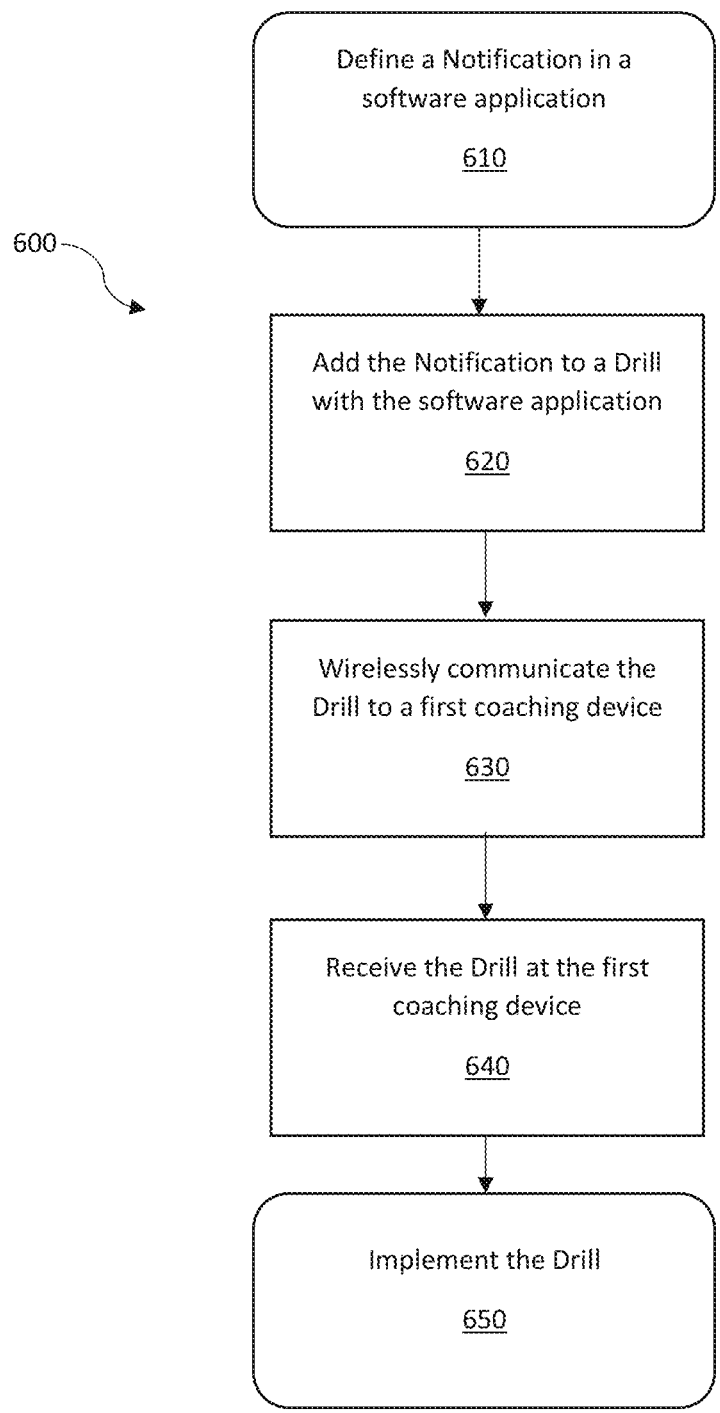
FIG. 6 illustrates an exemplary method for customizing a drill in a software application and implementing the drill on at least one coaching device in accordance with one embodiment.

FIG. 6 illustrates an exemplary method 600 for adding a drill in a software application and implementing the drill 660 on at least one coaching device 100 in accordance with some embodiments. In some embodiments, a user may begin to customize a drill by defining at least one coaching instruction in a software application 610. Defining the at least one coaching instruction includes adding user input in a software application to associate coaching feedback, including a coaching instruction, with a physical event detected by a sensor 204.

In embodiments, a user may select a standard Notification within the software application 610. Standard Notifications may be pre-defined in the software application and may not be editable by a user. However, a user may choose to not add the Notification to a Drill and may choose to not load a standard Drill on a coaching device 100.

In some embodiments, a user may choose to create a custom Notification with the software application 610. In some embodiments, the user may select an option to record a custom command from a list available on the interface of the software application. In some embodiments, a user may be able to categorize the Notification under a specific subset of notifications. For example, if the custom Notification were to relate to footwork, the user may swipe or otherwise select the category "Footwork" to categorize the new Notification. The user may select from a preset series of categories or may create their own categories of Notifications in some embodiments. In some embodiments, the user may be able to uniquely label the custom Notification and store the custom Notification in the software application. In some embodiments, the user may also specify the Tennis Event associated with the Notification. Users may also identify the speaker of the Notification and may later filter Drills and Lesson Plans associated with that speaker. In some embodiments, a user may also record an explanatory video associated with a Notification with the software application. The user may set this explanatory video as private or may allow others to access the explanatory video. In a similar fashion, a user may create custom Lesson Plans from a combination of standard and customized Drills through the software application. Drills may be added, deleted, and re-ordered in a Lesson Plan by a user at any time. A user may also copy Drills from one Lesson Plan to another and edit standard or user-created Drills to create new Drills in some embodiments.

In some embodiments, the user may associate the Notification with a sensor detection or calculated Tennis Event. For example, if the coaching device 100 were to detect the user's body position, the custom Notification "Aim with your body" may be associated with a sensor detecting the user having an improperly positioned body in step 620. A user may then choose to add this Drill to a Lesson Plan in step 620 or may choose to keep the Drill separate from a Lesson Plan.

In some embodiments, the user may then choose to wirelessly send the Drill or Lesson Plan to the coaching device 630. The coaching device may then receive the Drill 640. To send and receive Drills and Lesson Plans 630, 640, the user must first pair the coaching device 100 with the software application. In some embodiments, a user may be able to send a Lesson Plan or Drill from the software application by selecting options from the interface of the software application. The user may link the software application and coaching device 100 through Bluetooth or other wireless method, as would be understood by one of ordinary skill in the art. In some embodiments, the user must activate Bluetooth on the coaching device 100 by pressing and holding button 125. The software application may then detect the coaching device 100 and may display the detection on the interface of the software application. In some embodiments, a user may be able to name the coaching device 100 on the software application.

In some embodiments, the sending and receiving of a Drill or Lesson Plan may be optimized to reduce the amount of data transferred between the software application and the coaching device 100. Coaching instructions, for example, may be associated with large file sizes in some embodiments. Accordingly, when a Drill or Lesson Plan includes many different coaching instructions, the cumulative size of the corresponding files may be significant. To optimize the sending and receiving of a Drill or Lesson Plan, embodiments of the software application may create a manifest of the coaching instructions in a Drill or Lesson Plan, wherein each coaching instruction in the manifest is represented by a unique ID (generated, for example, by a hash algorithm or similar technique). Similarly, the coaching device 100 may maintain its own manifest of all the coaching instructions already stored on the coaching device 100 in some embodiments. Before the software application sends any coaching instructions, in some embodiments, it can query the coaching device 100's manifest to determine which coaching instructions it already has. In some embodiments, the software application may then send only the coaching instructions that are not already stored on coaching device 100.

The user may then implement the Drill associated with the Notification 650 at the coaching device 100. This implementation may be a single-user implementation shown in FIG. 5A or a multi-user implementation shown in FIG. 5B.

In some embodiments, the user may select a default voice to output a Notification. In other embodiments, a user may customize the voice to output a Notification.

In some embodiments, a user may want to add a new coaching instruction to a Drill that is already on coaching device 100 (i.e., without first creating or customizing a Drill or Notification in the software application). In some embodiments, the user may record an "on-the-fly" coaching instruction by pressing a button or combination/sequence of buttons on coaching device 100 and speaking into a microphone included in or connected to interface 202. In some embodiments, coaching device 100 may then automatically add the new, on-the-fly coaching instruction to the currently selected or in-progress Drill. In some embodiments, the user may then select to add the new coaching instruction to a Drill. The user may select to add the new coaching instruction to the currently selected or in-progress Drill or a second Drill.

The majority of the foregoing description is directed to a tennis embodiment, but other embodiments are also contemplated. For example, embodiments may be used in other paddle/racket sports (e.g., table tennis, racket ball, badminton, etc.). Embodiments may also be used when practicing or playing sports involving a club or stick (e.g., golf, baseball, cricket), whereby the coaching device 100 may be secured to or integrated within some portion of the club, stick, or other sporting device, or worn on the body of the player, and may provide feedback to the player. Such other embodiments may operate in the same or in similar fashion as the tennis embodiments, except that events are logically tied to aspects of the corresponding sport.

Some embodiments may be realized in hardware or a combination of hardware and software. Embodiments may be realized in a centralized fashion in one system, or in a distributed fashion where different elements are spread across several interconnected systems. Any kind of computer system or other apparatus adapted for carrying out the methods described herein is suitable. A typical combination of hardware and software can be a general-purpose computer system with a computer program that, when being loaded and executed, controls the system such that it carries out the methods described herein.

Some embodiments, as already noted above, may be embedded in a computer program product, such as a computer-readable storage medium or device which when loaded in a computer system is able to carry out the different methods described herein. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

Specific details are given in the description to provide a thorough understanding of example configurations (including implementations). However, configurations may be practiced without these specific details. For example, well-known circuits, processes, algorithms, structures, and techniques have been shown without unnecessary detail in order to avoid obscuring the configurations. This description provides example configurations only, and does not limit the scope, applicability, or configurations of the claims. Rather, the preceding description of the configurations will provide those skilled in the art with an enabling description for implementing described techniques. Various changes may be made in the function and arrangement of elements without departing from the spirit or scope of the disclosure.

Having described several example configurations, various modifications, alternative constructions, and equivalents may be used without departing from the spirit of the disclosure. For example, the above elements may be components of a larger system, wherein other rules may take precedence over or otherwise modify the application of various implementations or techniques of the present disclosure. Also, a number of steps may be undertaken before, during, or after the above elements are considered.

Having been provided with the description and illustration of the present application, one skilled in the art may envision variations, modifications, and alternate embodiments falling within the general inventive concept discussed in this application that do not depart from the scope of the following claims.

What is claimed is:

1. A first coaching device, comprising:
   an interface configured to:
      load a drill comprising at least one first coaching instruction;
      receive a first input from a user to select the drill; and
      output the at least one first coaching instruction;
   a sensor configured to measure an impact of a tennis ball on a racket;
   a wireless transceiver configured to:
      transmit at least one event message to at least one second coaching device, and
      receive at least one event message from the at least one second coaching device, wherein the at least one second coaching device is substantially similar to the first coaching device; and
   a processor configured to:
      communicate with the sensor, the wireless transceiver, and the interface;
      communicate with a software application configured to:
         receive a second user input to define the at least one first coaching instruction; and
         add the at least one first coaching instruction to the drill;
      download the drill to the first coaching device;
      select the at least one first coaching instruction based on the measured impact or at least one received event message;

instruct the wireless transceiver to transmit the at least one event message to the at least one second coaching device based on the impact of the tennis ball with the racket; and instruct the interface to output the at least one first coaching instruction.

2. The first coaching device of claim 1 wherein the first coaching device is configured to be worn on a wrist of the user.

3. The first coaching device of claim 1 wherein measuring the impact includes measuring at least one of position, direction of motion, speed of motion, acceleration, vibration, and shock.

4. The first coaching device of claim 1 wherein:
the drill further comprises at least one second coaching instruction;
the first coaching instruction corresponds to the measured impact; and
the second coaching instruction corresponds to the received event message.

5. The first coaching device of claim 1 wherein the interface is configured to record at least one second coaching instruction; and wherein the processor is configured to add the at least one second coaching instruction to the drill.

6. The first coaching device of claim 1 wherein the processor is further configured to create and maintain a manifest of coaching instructions stored on the first coaching device; and
wherein downloading the drill to the first coaching device comprises downloading only coaching instructions not already stored on the first coaching device.

7. The first coaching device of claim 1 wherein the processor is further configured to select the at least one first coaching instruction based on the drill.

8. The first coaching device of claim 7 wherein the drill defines at least one of the frequency or order at which the processor selects the at least one first coaching instruction.

9. A computer-implemented method for providing at least one coaching instruction via a coaching device, comprising:
defining the at least one coaching instruction in a software application via a first user input;
adding, via the software application, the at least one coaching instruction to a drill;
downloading the drill to a first coaching device;
receiving, at the first coaching device, the drill;
receiving, at the first coaching device, a second user input to select the drill;
measuring, at the first coaching device, an impact of a tennis ball with a tennis racket;
calculating, at the first coaching device, at least one physical parameter associated with the tennis racket;
translating, at the first coaching device, the at least one physical parameter to a physical event;
selecting, at the first coaching device, the at least one coaching instruction based on the physical event;
outputting, at the first coaching device, the at least one coaching instruction;
transmitting an event message associated with the physical event from the first coaching device to a second coaching device;
receiving the event message from the first coaching device at the second coaching device;
selecting, at the second coaching device, a second at least one coaching instruction based on the event message; and
outputting, at the second coaching device, the second at least one coaching instruction.

10. The method of claim 9 further comprising recording, at the first coaching device, a second coaching instruction and adding the second coaching instruction to the drill.

11. The method of claim 9 further comprising creating and maintaining, at the first coaching device, a manifest of coaching instructions stored on the first coaching device; and wherein downloading the drill to the first coaching device comprises downloading only coaching instructions not already on stored on the first coaching device.

12. The method of claim 9 wherein selecting, at the first coaching device, the at least one coaching instruction is further based on the drill.

13. The method of claim 12 wherein the drill defines at least one of the frequency or order at which the at least one coaching instruction is selected at the first coaching device.

14. The method of claim 12 wherein the drill comprises a defined duration of time during which the at least one coaching instruction is selected.

15. A coaching system, comprising:
a software application configured to:
receive a first user input to define at least one coaching instruction; and
add the at least one coaching instruction to a drill; and
a coaching device, comprising:
an interface configured to:
load the drill comprising the at least one coaching instruction;
receive a second user input to select the drill; and
output the at least one coaching instruction;
a sensor configured to measure impact of a tennis ball on a racket;
a wireless transceiver configured to:
transmit at least one event message to at least one other coaching device, and
receive at least one event message from the at least one other coaching device, wherein the at least one other coaching device is substantially similar to the coaching device; and
a processor configured to:
communicate with the sensor, the wireless transceiver, and the interface;
communicate with the software application;
select the at least one coaching instruction based on the measured physical impact or at least one received event message;
download the drill to the coaching device;
instruct the wireless transceiver to transmit the at least one event message to at least one coaching device based on the impact of the tennis ball with the racket; and
instruct the interface to output the at least one coaching instruction.

16. The system of claim 15 wherein the drill comprises at least one first coaching instruction and at least one second coaching instruction; and
wherein the first coaching instruction corresponds to the measured physical impact and the second coaching instruction corresponds to the received event message.

17. The system of claim 15 wherein the processor is further configured to create and maintain a manifest of coaching instructions stored on the coaching device; and wherein downloading the drill to the coaching device comprises downloading only coaching instructions that are not already stored on the coaching device.

18. The system of claim 15 wherein the processor is further configured to select the at least one coaching instruction based on the drill.

19. The system of claim 18 wherein the drill defines at least one of the frequency or order at which the processor selects the at least one coaching instruction.

20. The system of claim 15 wherein the interface is further configured to record a second coaching instruction; and wherein the processor is further configured to add the second coaching instruction to the drill.

\* \* \* \* \*